United States Patent [19]

Andersson

[11] Patent Number: 4,671,265
[45] Date of Patent: Jun. 9, 1987

[54] EARPLUG DEVICE

[75] Inventor: Lars-Gunnar L. Andersson, Höganäs, Sweden

[73] Assignee: Bilsom AB, Billeshohm, Sweden

[21] Appl. No.: 801,958

[22] Filed: Nov. 26, 1985

[30] Foreign Application Priority Data

Nov. 29, 1984 [SE] Sweden .................................. 8406042

[51] Int. Cl.$^4$ ...................... A61F 11/02; A61F 11/00; A42B 1/06
[52] U.S. Cl. ........................................ 128/152; 2/209; 128/151
[58] Field of Search ..................... 128/152, 151; 2/209, 2/209.1, 423; 181/130, 131, 135

[56] References Cited

U.S. PATENT DOCUMENTS

| 968,008 | 8/1910 | Waller | 128/152 |
|---|---|---|---|
| 997,673 | 7/1911 | Heggf | 128/152 |
| 2,670,737 | 3/1954 | Cantor | 128/152 |
| 3,301,253 | 1/1967 | Glorig | 128/152 |
| 4,314,553 | 2/1982 | Westerdal | 128/152 |
| 4,490,857 | 1/1985 | Leight et al. | 128/152 X |

FOREIGN PATENT DOCUMENTS 0025644 12/1935 Australia .............................. 128/152

Primary Examiner—Robert A. Hafer
Assistant Examiner—Kathleen J. D'Arrigo
Attorney, Agent, or Firm—Burns, Doane, Swecker & Mathis

[57] ABSTRACT

An earplug device includes a headband with earplugs attached to the ends thereof. The earplugs have a head portion and a shank portion, the latter with its rear end joined to the associated headband end. The shank portion has a stiffened middle section and is articulately connected on either side thereof respectively to the head portion and headband end to form a doubly articulated shank configuration. The head portion is thus given the opportunity of coacting in the best possible way with the auditory canal of an ear, and to a substantial degree independently of the attitude of the headband.

12 Claims, 3 Drawing Figures

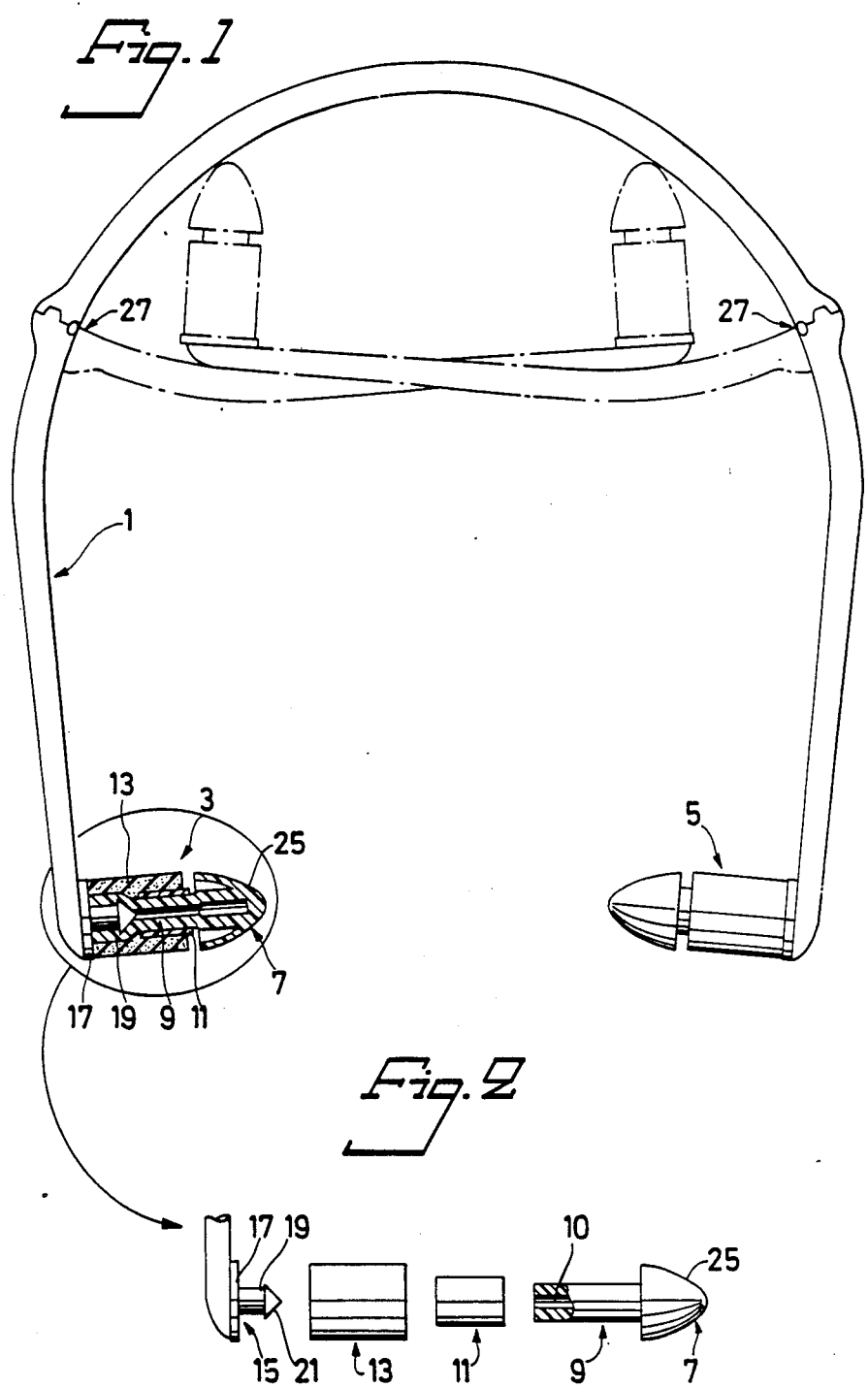

EARPLUG DEVICE

TECHNICAL FIELD

The present invention relates to an earplug device of the kind including two earplugs and an elastic headband, an earplug being connected to each end of the headband, each earplug including a shank portion with its rear end connected to the headband and its forward end provided with a head portion adapted for coaction with the auditory canal of an ear for the purpose of sealing or closing off the canal.

BACKGROUND ART

Earplugs provided with shanks are known in many different embodiments. It is often desirable to have such earplugs connected to each other in pairs, e.g. by a string or the like. An example of this is illustrated in our own U.S. Pat. No. 4,314,553.

It has furthermore been known for a long time to arrange earplugs in pairs on an elastic headband. In such a case as well, the earplugs can include a shank portion, which is connected to the headband. An example of this is illustrated in U.S. Pat. No. 3,618,600. Another example is illustrated in U.S. Pat. No. 4,461,290, disclosing an earplug connection involving a ball joint.

However, it has often been found difficult to obtain satisfactory sealing or closing-off of the auditory canal with earplugs carried by a headband.

OBJECT OF THE INVENTION

The main object of the present invention is therefore to provide an earplug device of the kind mentioned in the introduction, with which there are enabled improved sealing and sealing-off effects.

A further object of the invention is to provide an earplug device of the kind mentioned, that includes earplugs with a head portion of the general embodiment illustrated in our above-mentioned U.S. Pat. No. 4,314,553.

SUMMARY OF INVENTION

The above-mentioned objects are achieved by an earplug device that has the distinguishing features defined in the claims.

The inventive earplug device is thus essentially distinguished in that the shank portion of the respective earplug is stiffened and connected both to the head portion and to the headband in a manner such as to provide articulation, thus forming a doubly articulated shank configuration. The term "articulation" is here to be given wide meaning and does not require the arrangement of special articulation means.

The doubly articulated shank configuration in accordance with the invention has been found to result in that the head portion of the respective earplug, coacting with the auditory canal, may easily and effectively be caused to assume the best position from the sealing or closing-off aspect by the legs or side portions of the headband being moved somewhat backwards and forwards while a light inward pressure is applied to them. The best position thus obtained will then remain, at least substantially, and essentially independent of unavoidable small movements of the headband. This effect is not obtained with prior art earplugs carried by a headband.

According to the invention, it is preferred to have at least substantially equal articulations at the two ends of the shank portion.

The articulation in accordance with the invention is advantageously achieved by the material in the respective shank end and/or in connecting parts of the device being so elastic in relation to remaining connection material that bending primarily takes place here. According to a preferred embodiment, the shank portion may thus include a stiff middle section in association with substantially less stiff end sections, which will consequently be relatively flexible and deflectable, these sections being connected to the head portion of the earplug and the headband, respectively.

Although the shank portion, which is preferably integral with its associated head portion, could have an integrated, stiffer middle section, it is in accordance with the invention advantageous to let the shank portion include a shaft section of elastic material with a middle portion stiffened by one or more separate stiffening members. The latter may advantageously comprise a stiffer tubular sleeve or the like, surrounding the middle portion of the shaft section, the sleeve thus leaving end portions of the shaft section free to function as articulation elements.

It has been found particularly advantageous to have a tubular shaft section, i.e. one with a central bore. There is thus achieved very good articulation on both sides of the stiffened middle section.

The utilisation of a tubular shaft section also involves that connection to the headband can be accomplished in a very advantageous manner, namely by using a pin or the like, projecting from the headband and into the bore of the shaft section. The pin suitably enters as far as the vicinity of the zone where the shank portion stiffening starts, so that a welldefined articulation zone is obtained. Particularly advantageous is that the diameter of the pin is greater than that of the bore, so that the headband end portion of the shaft section will be expanded, articulation then being clearly pronounced just where the expansion begins.

Although the head portion of the respective earplug can be conceived as being implemented in many different ways, depending on the desired coaction with the auditory canal, it has been found advantageous to implement the head portion at least substantially in the way described in our previously mentioned U.S. Pat. No. 4,314,553, the contents of which are to be regarded as incorporated in this application by reference thereto.

The head portion in other words preferably includes an essentially conically shaped, hollow wall element, the apex portion of which is internally joined to, or merges with, the forward end of the shank portion, the wall element extending backwards over the shank portion and separate from it, there being spacer members distributed circumferentially between the inner surface of the wall element and the shank portion. Advantageously the spacer members are lamella-like and extend in the direction of the shank in radial planes suitably distributed round the shank portion. The latter, with its middle section which is to be stiffened in accordance with the invention, the wall element and the spacer members are advantageously fabricated integrally from an elastic material, such as a suitable soft plastics. According to the invention it is suitable to stiffen the shank portion up to the vinicity of the spacer members, so that there is a pronounced articulation zone here as well.

In continuation, the invention will be described in more detail with the aid of an embodiment and with reference to the accompanying drawings.

BRIEF DESCRIPTION OF DRAWINGS

FIG. 1 is a schematic view of an embodiment of the inventive earplug device, one earplug being shown in an axial, longitudinal section, the device also being shown by chain-dotted lines in a folded state.

FIG. 2 is an exploded view further illustrating the construction of the earplug and its attachment to the associated headband end.

DESCRIPTION OF THE PREFERRED EMBODIMENT

Figure 3:
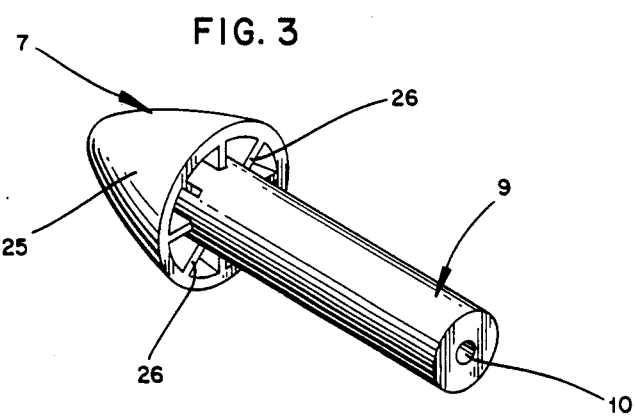
FIG. 3 is a perspective view of the head and shank portions of the earplug of FIGS. 1 and 2.

The inventive earplug device illustrated in FIGS. 1 and 2 includes a foldable headband 1, at either end of which respective earplugs 3 and 5 are connected. Each earplug comprises a head portion 7 with an integral stem-like shank portion 9, both of soft, elastic plastics material, a tubular stiffening sleeve 11 of stiff plastics and an outer foamed plastics protection muff 13. The shank porton 9 is tubular with a central, longitudinal bore 10, which is open at the free rear end of the shank portion.

For the attachment of an earplug the respective headband end is provided with a mounting member 15 including a supporting boss 17 on the inside, from the middle of which an attachment pin 19 projects at right angles inwardly, i.e. towards the other headband end. The pin 19, which has its forward end 21 conical and formed as a latching member, extends substantially at right angles to the direction of the headband end and is intended to be thrust into the bore 10 in the shank portion 9 and be retained therein.

In assembling the earplug device in accordance with the invention, the stiffening sleeve 11 is first mounted on the shank portion 9. The inside diameter of the sleeve corresponds to the outside diameter of the shank portion 9 such that the sleeve sits on the shank portion with a good fit. The forward edge of the sleeve 11 is brought to lie flush with the rear edge of the head portion 7. The protective muff 13 is now placed outside the shank portion 9 and sleeve 11. The pin 19 is then inserted in the bore 10 until the rear end of the shank portion engages against the boss 17. The pin 19 has a larger diameter than that of the bore 10, the end section of the shank portion thus expanding round the pin 19, and this in combination with the latching function of the pin makes the fixture very good. The lengths of the pin 19, sleeve 11 and shank portion 9 behind the head portion 7 are selected such that the rear portion of the sleeve 11 lies immediately in front of, or flush with the tip of the pin 19, there thus being obtained a well-defined articulation zone just between the pin and the sleeve. The articulation zone thus coincides with the region where the material in the shank portion begins to expand conically.

The pin diameter is selected such that the outside diameter of the expanded, affixed shank end section is substantially the same as the outside diameter of the sleeve 11. The outer protective muff of soft foamed plastics is thrust over so that it covers the expanded shank portion and at least the major part of the sleeve 11.

The integrated combination of the head portion 7 and shank portion 9, excepting the hole or bore 10, is implemented in accordance with what is described in our previously mentioned U.S. Pat. No. 4,314,553. The head portion thus includes a substantially conical, hollow wall element 25, with its apex portion internally joined to the forward end of the shank portion 9. The wall element extends backwards over the shank portion and spaced therefrom. Referring to FIG. 3, between the inner surface of the wall element 25 and the circumferential surface of the shank portion there extend integrated lamella-like spacer members 26 with extension in the shank direction in radial planes distributed round the shank portion. The rear edge of the spacer members is flush with the rear edge of the wall element 25. The sleeve 11 extends forwards to the vicinity of the rear edges of the spacer members such as to form an articulation zone here.

The described, inventive earplug device is foldable insofar as the headband 1 is provided with articulation members 27 on either leg side, enabling the lower leg portions of the headband to be folded towards each other, as illustrated by the chain-dotted lines in FIG. 1.

The invention is of course not restricted to the illustrated and described embodiment, and variations and modifications are possible within the scope of the invention as it is defined in the following claims.

What is claimed is:

1. Earplug device including two earplugs and an elastic headband, each earplug connected to an end portion of the headband and each earplug including a shank member having a rear end portion connected to one of the end portions of the headband, a flexible second portion adjacent said rear end portion, a flexible forward end portion provided with a head portion arranged for coaction with the auditory canal of an ear for closing off said canal and a stiffened middle portion between said flexible second portion and said flexible forward end portion so that said shank member is articulated by both said second portion and said forward end portion, thus forming a doubly articulated shank configuration.

2. Earplug device as claimed in claim 1, wherein the shank member is in the form of a flexible shaft of elastic material with the middle portion of the shank member stiffened by stiff, tubular sleeve means surrounding the middle portion, the flexible second and forward end portions of the shank member extending beyond opposite ends of said tubular sleeve means, said flexible forward end and rear end portions being respectively connected to the head portion and the headband such that articulation is obtained at said forward end and second portions of the shank member.

3. Earplug device as claimed in claim 2, wherein the shank member is tubular and has a central bore.

4. Earplug device as claimed in claim 3, wherein the shank member is connected to the headband with pin means projecting from the headband and extending into the bore at the rear end portion of the shank member up to a location adjacent an end of the sleeve means facing the headband end portion, said flexible second portion disposed between said location of the pin means and said end of the sleeve means facing the headband end portion.

5. Earplug device as claimed in claim 4, wherein the pin means has a diameter greater than that of the bore, so that the rear end portion of the shank member is expanded, the end of the sleeve means facing the headband being proximal to the expanded end portion of the shank member.

6. Earplug device as claimed in claim 4, wherein the head portion includes a generally conical, hollow wall element with its apex portion joined to the forward end of the shank member, the wall element having a wall portion extending rearwardly over the shank member and being radially spaced therefrom, said head portion including spacer members distributed circumferentially between an inner surface of the wall element and the shank member.

7. Earplug device as claimed in claim 3, wherein the head portion includes a generally conical, hollow wall element with its apex portion joined to the forward end of the shank member, the wall element having a wall portion extending rearwardly over the shank member and being radially spaced therefrom, said head portion including spacer members distributed circumferentially between an inner surface of the wall element and the shank member.

8. Earplug device as claimed in claim 7, wherein the spacer members are lamella-like and extend in the direction of the shank member in radial planes.

9. Earplug device as claimed in claim 8, wherein the forward end portion of the shank member, the wall element and the spacer members are integrally formed from an elastic material.

10. Earplug device as claimed in claim 9, wherein a forward end of the stiffened middle portion is located proximal to the spacer members.

11. Earplug device as claimed in claim 9, wherein the elastic material is soft plastic.

12. Earplug device as claimed in claim 1, wherein the shank member is tubular and has a central bore.

* * * * *